(12) United States Patent
Steinberg

(10) Patent No.: US 6,304,628 B1
(45) Date of Patent: Oct. 16, 2001

(54) WEDGE ANGLE OPTIMIZATION FOR A VIRTUAL WEDGE TREATMENT

(75) Inventor: Todd H. Steinberg, Antioch, CA (US)

(73) Assignee: Siemens Medical Systems, Inc., Iselin, NJ (US)

(*) Notice: Subject to any disclaimer, the term of this patent is extended or adjusted under 35 U.S.C. 154(b) by 0 days.

(21) Appl. No.: 09/251,705

(22) Filed: Feb. 17, 1999

(51) Int. Cl.[7] .................................................... A61N 5/10
(52) U.S. Cl. ............................................. 378/65; 378/108
(58) Field of Search ................................... 378/65, 64, 68, 378/91, 97, 95, 108, 145, 146, 147, 156, 151, 152; 250/505.1, 492.1, 492.3

(56) References Cited

U.S. PATENT DOCUMENTS

| 5,148,032 | 9/1992 | Hernandez . |
| 5,563,925 | 10/1996 | Hernandez . |
| 5,668,847 | 9/1997 | Hernandez . |
| 5,847,403 | * 12/1998 | Hughes et al. ..................... 250/505.1 |

* cited by examiner

Primary Examiner—David P. Porta

(57) ABSTRACT

Aspects for virtual wedge treatment with wedge angle optimization are described. In a method aspect, the method includes adjusting a preselected calibration factor based on chosen treatment conditions. The method further includes achieving an optimal wedge intensity distribution with the adjusted calibration factor for the chosen treatment conditions in a virtual wedge radiation treatment session. Additionally, adjusting includes determining an appropriate calibration factor for a given wedge angle and depth.

13 Claims, 3 Drawing Sheets

WEDGE ANGLE OPTIMIZATION FOR A VIRTUAL WEDGE TREATMENT

FIELD OF THE INVENTION

The present invention relates to radiation treatment devices, and more particularly, to wedge angle optimization for a virtual wedge treatment with a radiation treatment device.

BACKGROUND OF THE INVENTION

Radiation-emitting devices are generally known and used for radiation therapy in the treatment of patients, for example. Typically, a radiation therapy device includes a gantry which can be swiveled around a horizontal axis of rotation in the course of a therapeutic treatment. A linear accelerator is located in the gantry for generating a high-energy radiation beam for therapy. This high radiation beam can be an electron radiation or photon (X-ray) beam. During treatment, the radiation beam is provided on one zone of a patient lying in the isometer of gantry rotation.

The goal of radiation treatment planning is to maximize the dose to the target volume while protecting radiation-sensitive healthy tissue. The X-ray beam intensity often varies over the treatment field by placing an X-ray absorber in the beam's path. This allows the target volume to be placed in regions of high beam intensity, while the surrounding radiation-sensitive tissue is protected by placement in low intensity regions. A simple example is a wedge-shaped isodose distribution, which has been found to be clinically useful in treatment plans.

One frequently used method is to place a physical wedge accessory (i.e., a wedge-shaped absorber) in the X-ray beam path that exponentially decreases the beam intensity laterally across the treatment field. A desirable wedgeshaped isodose distribution results. The "toe" of the wedge (i.e., where the thickness of the wedge is the smallest) produces the high beam intensity region, since this portion of the beam has the least attenuation.

The use of the physical wedge accessory has some negative side effects, however. The primary beam intensity is reduced at the target volume; thus, treatment times are increased. Further, scattering of the beam outside the treatment field causes additional dose to be delivered outside the target volume. It also introduces a spatial energy dependence (i.e., hardness) to the beam, affecting the depth at which the radiation is absorbed across the treatment field. Additional time and effort are required to design, validate, manufacture, install remove, and store the accessories. In addition, only a limited number of wedge angles are available.

The virtual wedge function integrated into some treatment devices, such as MEVATRON and PRIMUS systems from Siemens Medical Systems-Oncology Care Systems, Concord, Calif., is used to achieve an accumulated dose profile and isodose distribution similar to that of a physical wedge accessory. The virtual wedge function is accomplished by controlling the travel of a secondary collimator jaw and the X-ray beam intensity during irradiation. The virtual wedge scheme eliminates most of the problems associated with the physical wedge. However, some problems still exist in getting a uniform dose at a desired depth.

An example of wedge isodose distributions is shown in FIG. 1. Wedge angles for wedge isodose distributions are presently defined at a 10 cm (centimeter) depth based on where the isodose crosses the central axis. A line drawn tangent to the isodose defines the nominal wedge angle ($\alpha$). Virtual wedge treatments regularly use the 10 cm depth in defining the wedge angle. But, treatment areas are often at different depths, such as 5 cm, which affects the dose distribution, but which is not readily accommodated in the virtual wedge treatment to ensure uniform dose delivery.

Accordingly, what is needed is a method and system for optimizing wedge angles in a virtual wedge treatment.

SUMMARY OF THE INVENTION

The present invention provides method and system aspects for virtual wedge treatment with wedge angle optimization. In a method aspect, the method includes adjusting a preselected calibration factor based on chosen treatment conditions. The method further includes achieving an optimal wedge intensity distribution with the adjusted calibration factor for the chosen treatment conditions in a virtual wedge radiation treatment session. Additionally, adjusting includes determining an appropriate calibration factor for a given wedge angle and depth.

Through the present invention, an improved ability to optimize a virtual wedge treatment for a given therapy session is achieved. The aspects of the present invention readily provide an appropriate calibration factor for desired wedge angles and depths to readily adjust wedge intensity distribution for an optimal therapy session. These and other advantages of the aspects of the present invention will be more fully understood in conjunction with the following detailed description and accompanying drawings.

DETAILED DESCRIPTION OF THE INVENTION

The present invention relates to wedge angle optimization within a virtual wedge treatment. The following description is presented to enable one of ordinary skill in the art to make and use the invention and is provided in the context of a patent application and its requirements. Various modifications to the preferred embodiment will be readily apparent to those skilled in the art and the generic principles herein may be applied to other embodiments. In the following, the invention is described with primary reference to a system for delivering X-ray radiation to a field of a patient, and for delimiting the field using at least one movable plate in the beam path from a radiation source. This is by way of example. Thus, the present invention is not intended to be merely limited to the embodiment shown but is to be accorded the widest scope consistent with the principles and features described herein.

Figure 2:
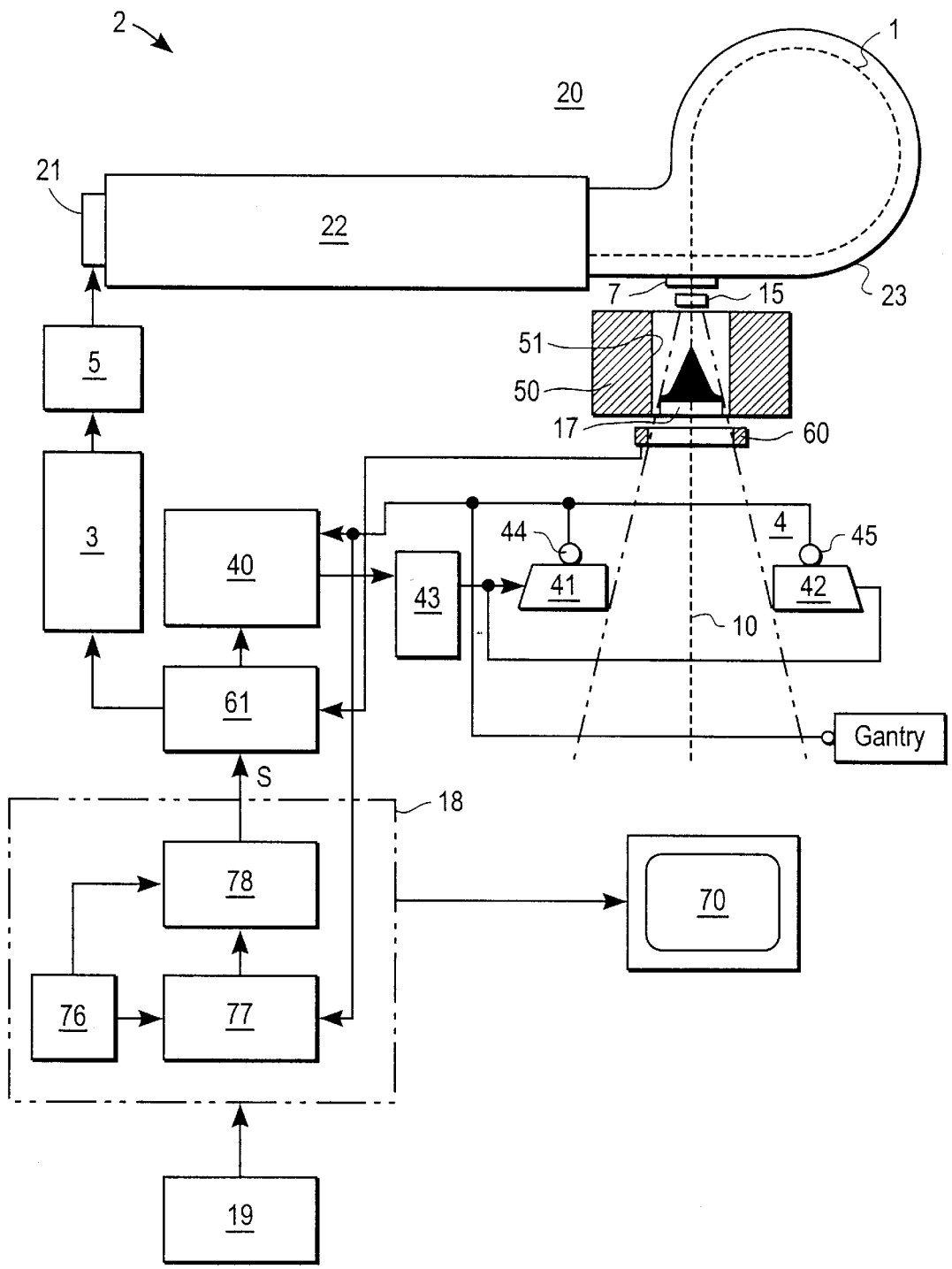
FIG. 2 is a block diagram illustrating portions of a processing unit, control unit, and a beam generation system in a radiation treatment device for a preferred embodiment of the present invention.

FIG. 2 shows a portion of an illustrative radiation treatment device 2 and portions of a treatment processing unit in detail. An electron beam 1 is generated in an electron accelerator 20. Accelerator 20 comprises an electron gun 21, a wave guide 22, and an evacuated envelope or guide magnet 23. A trigger system 3 generates injector trigger signals and supplies them to injector 5. Based on these injector trigger signals, injector 5 generates injector pulses which are fed to electron gun 21 in accelerator 20 for generating electron beam 1. Electron beam 1 is accelerated and guided by wave guide 22. For this purpose, a high frequency (HF) source (not shown) is provided which supplies radio frequency (RF) signals for the generation of an electromagnetic field supplied to wave guide 22. The electrons injected by injector 5 and emitted by electron gun 21 are accelerated by this electromagnetic field in wave guide 22 and exit at the end opposite to electron gun 21 as electron beam 1. Electron beam 1 then enters a guide magnet 23, and from there is guided through a window 7 along axis 10. After passing through a target 5, the beam goes through a passageway 51 of a shield block 50 and encounters a flattening filter 17. Next, the beam is sent through a measuring chamber 60, in which the dose is ascertained. If the scattering foils are replaced by a target, the radiation beam is an X-ray beam.

Plate arrangement 4 comprises a pair of aperture plates 41 and 42 and an additional pair of aperture plates (not shown) arranged perpendicular to plates 41 and 42. In order to change the size of the irradiated field, the aperture plates 41 and 42 can be moved with respect to axis 10 by a drive unit 43. Drive unit 43 comprises an electric motor which is coupled to plates 41 and 42 and which is controlled by a motor controller 40. Position sensors 44 and 45 are also coupled to plates 41 and 42, respectively, for sensing their positions.

The area of a patient that is irradiated is known as the field. As is well known, plates 4 are substantially impervious to the emitted radiation. They are mounted between the radiation source and patient in order to delimit the field. Areas of the body, for example, healthy tissue, are therefore subjected to as little radiation as possible, and preferably to none at all. As previously described, with at least one of the plates movable, the distribution of radiation over the field need not be uniform (i.e., one region can be given a higher dose than another); further, with the gantry able to be rotated, different beam angles and radiation distributions are allowed without having to move the patient around.

A central treatment processing or control unit is usually located apart from radiation treatment device 2 in a different room to protect the therapist from radiation. Treatment processing unit includes an output device, such as at least one visual display unit or monitor 70, and an input device, such as a keyboard 19, although data can be input also through data carriers, such as data storage devices. The treatment processing unit is typically operated by the therapist who administers actual delivery of a radiation treatment as prescribed by an oncologist. By utilizing keyboard 19, or other input device, the therapist enters into a control unit 76 of the treatment processing unit the data that defines the radiation to be delivered to the patient. On the screen of a monitor 70, various data can be displayed before and during the treatment.

Central processing unit 18, included in treatment processing unit, is connected with the input device, e.g., keyboard 19, for inputting the prescribed delivery of the radiation treatment and with a dose control unit 61 that generates the desired values of radiation for the controlling trigger system 3. Trigger system 3 suitably adapts the pulse repetition frequency or other parameters to change the radiation output. A digital dosimetry system is particularly advantageous in order to more easily control the digital output of central processing unit 18. Central processing unit 18 suitably includes a control unit 76 for controlling execution of the treatment program in conjunction with memory 77 and a combination circuit 78 which suitably receives signals from the control unit 76 and memory 77 for combination to produce a set signal, S, that identifies a dose rate for dose rate control unit 61.

In accordance with the present invention, the control unit 76 is utilized to produce optimum wedge angles during a virtual wedge treatment for a given depth of treatment. The optimization of wedge angles in accordance with the present invention utilizes a virtual wedge algorithm: $I = e^{-c\mu(\tan\alpha)D}$, where I represent wedge intensity distribution or the intensity value as a function of jaw position and beam profile, c represents a scaling factor, which in conventional practice has been a constant, preset value established by the treatment device manufacturer, p represents a mean linear attenuation coefficient, a represents the wedge angle, and D represents the jaw position.

Figure 1:
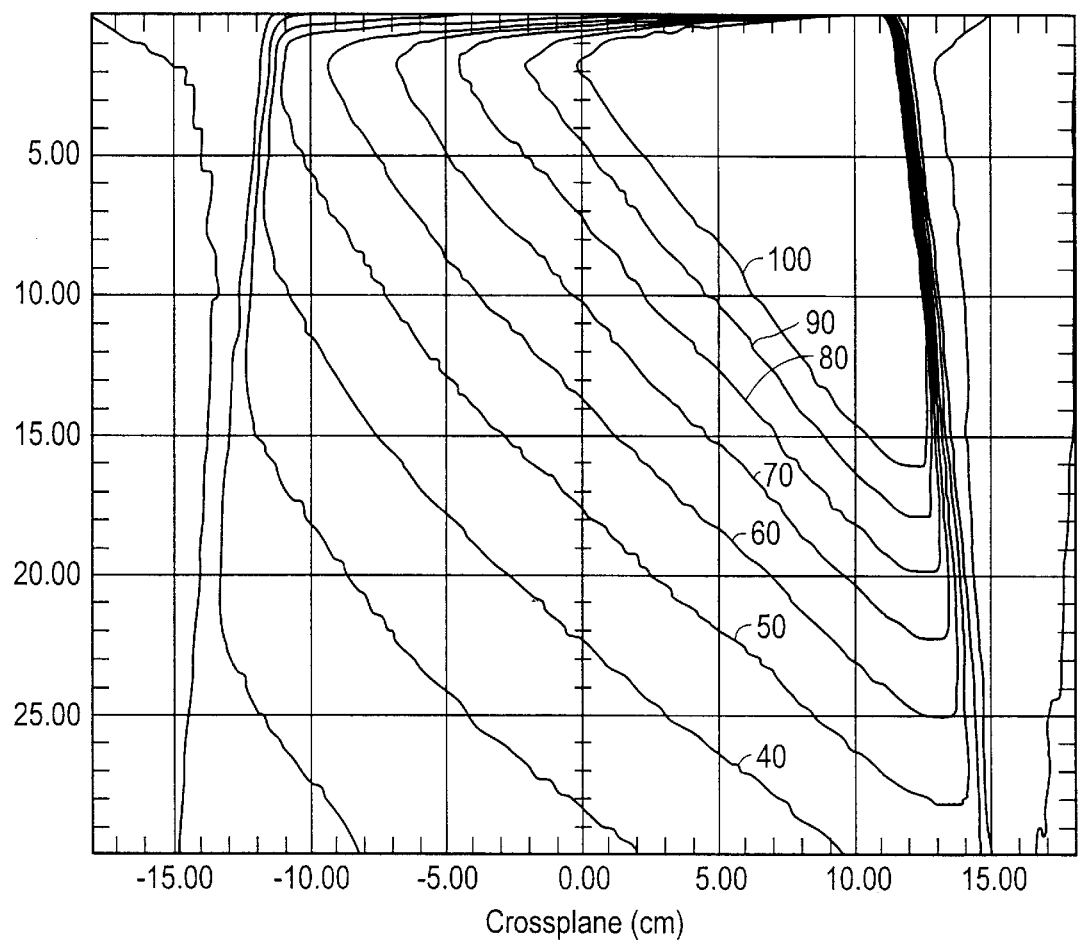
FIG. 1 illustrates an example of wedge isodose distributions for defining a wedge angle.
Figure 3:
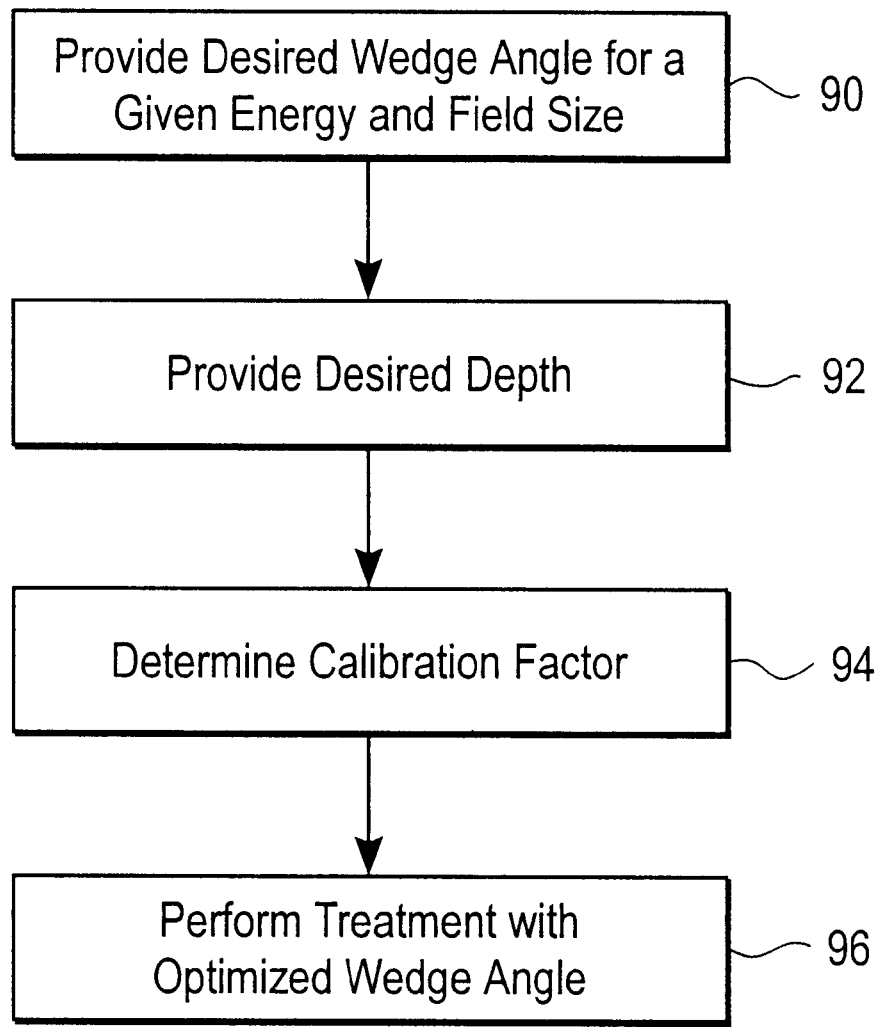
FIG. 3 illustrates a block flow diagram for a wedge angle optimization process in accordance with the present invention.

As represented by the graph of FIG. 1, in an isodose distribution, a nominal wedge angle varies among given depths. The present invention readily achieves utilization of an optimal wedge angle for a given depth by controlling changes in the coefficient 'c' via control unit 76. An overall block diagram of a process for the present invention is illustrated in FIG. 3. The process initiates with a user providing a desired wedge angle (step 90) and a desired depth (step 92). For example, the values for the desired wedge angle and desired depth are input via keyboard 19 by entering specific values into an input screen. Of course, other forms of input may be used, as desired. Once the wedge angle and depth are provided, a calibration factor value, 'c', is determined (step 94).

The calibration factor is capably determined based on information provided in memory 77, e.g., in a look-up table. The values of the calibration factor are suitably provided by a machine calibration routine. For example, a value is selected for the calibration factor. A monitored virtual wedge treatment then proceeds using the calibration factor value for a chosen wedge angle and depth. The wedge angle is then measured at the given depth. The measured values are then compared with desired dose distributions, i.e., the isodose profiles generated if the radiation output were held constant and a physical wedge were included in the beam path. If the measured wedge angle matches the chosen wedge angle, then the calibration value is correct. The calibration values may then be stored as entries in a look-up table. If the measured angle is not correct, then the calibration value is adjusted and the values are then remeasured. The iterative process proceeds until appropriate results occur for each of the combinations of calibration values, wedge angles, and depths.

With the calibration value determined, the virtual wedge treatment is then performed (step 96). The use of the appropriate calibration value coefficient adjusts the virtual wedge treatment to the desired wedge angle for the given depth. A more uniform dose distribution results for individual treatments and improves radiation therapy by more closely conforming to the treatment conditions, e.g., the contour of the patient being treated.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for virtual wedge treatment with wedge angle optimization, the method comprising the steps of:
   a) adjusting a preselected calibration factor based on chosen treatment conditions; the adjusting step further comprises the step of (a1) determining an appropriate calibration factor for a given wedge angle and depth; and
   b) achieving an optimal wedge intensity distribution with the adjusted calibration factor for the chosen treatment conditions in a virtual wedge radiation treatment session.

2. The method of claim 1 wherein the achieving step (b1) further comprises the step of achieving an optimized wedge angle.

3. The method of claim 1 wherein the determining step (a1) further comprises the step of performing a calibration routine over a range of wedge angles, field sizes and depths, for a given energy to determine the appropriate calibration factor for each given wedge angle field size and depth for a given energy.

4. The method of claim 1 wherein the determining step (a1) further comprises the step of retrieving the appropriate calibration factor stored for the given wedge angles field size and depth, for a given energy.

5. A system for providing a virtual wedge treatment with wedge angle optimization, the system comprising:
   a radiation treatment device for providing radiation therapy; and
   a control unit coupled to the radiation treatment device for controlling the radiation therapy by adjusting a preselected calibration factor based on chosen treatment conditions, and achieving an optimal wedge intensity distribution with the adjusted calibration factor for the chosen treatment conditions in a virtual wedge radiation treatment session;
   wherein the control unit further determines an appropriate calibration factor for a given wedge angle field size and depth, for a given energy.

6. The system of claim 5 wherein the control unit further achieves an optimized wedge angle.

7. The system of claim 5 wherein the radiation therapy device and control unit further perform a calibration routine over a range of wedge angles, field sizes and depths, for a given energy to determine the appropriate calibration factor for each given wedge angle, field size and depth, for a given energy.

8. The system of claim 5 further comprising memory coupled to the control unit for storing the appropriate calibration factor.

9. The system of claim 5 further comprising an input device for inputting the given wedge angle and depth.

10. A method for providing wedge angle optimization during virtual wedge radiation treatment, the method comprising the steps of:
   a) providing a desired wedge angle and depth for a given energy and field size for a virtual wedge treatment session;
   b) determining a calibration factor corresponding to the desired wedge angle, field size, energy and depth; and
   c) performing the virtual wedge treatment session, wherein the determined calibration factor adjusts wedge intensity distribution to achieve wedge angle optimization.

11. The method of claim 10 wherein the determining step (b) further comprises the step of (b1) performing a calibration routine to establish appropriate calibration factors over a range of wedge angles, field size and depth value combinations for a given energy.

12. The method of claim 11 wherein the determining step (b) further comprises the step of (b2) providing an appropriate calibration factor for the desired wedge angle, field size and depth, for a given energy from the established appropriate calibration factors.

13. The method of claim 10 wherein the performing step (c) further comprises the step of adjusting a radiation beam output while adjusting positioning of at least one dynamic collimator jaw relative to at least one stationary collimator jaw.

* * * * *